United States Patent [19]

Walthour

[11] Patent Number: 5,312,324
[45] Date of Patent: May 17, 1994

[54] NASAL DRESSING SYSTEM

[76] Inventor: Charles D. Walthour, 5203 Acorn Trail, Dallas, Ga. 30132

[21] Appl. No.: 944,962

[22] Filed: Sep. 15, 1992

[51] Int. Cl.⁵ .................. A62B 7/10; A61F 13/00; A61F 15/00; A61L 15/00
[52] U.S. Cl. ...................... 602/74; 602/79; 602/60; 602/61; 602/41; 128/206.18
[58] Field of Search ........ 604/358, 393, 391, 396–402; 602/41–47, 60–61, 74, 79; 128/95.1, 97.1, 99.1–101.1, 106.1–107.1, 112.1, 116.1, 121.1–124.1, 205.27, 205.28, 205.29, 206.12, 206.8, 206.21, 206.22; 24/17 B, 31 C

[56] References Cited

U.S. PATENT DOCUMENTS

| | | |
|---|---|---|
| 2,064,986 | 12/1936 | Mezz . |
| 2,087,042 | 7/1937 | Phillips ............................ 128/206.18 |
| 2,161,607 | 6/1939 | Anderson ....................... 128/206.18 |
| 2,295,321 | 9/1942 | Anderson ....................... 128/206.18 |
| 2,361,506 | 10/1944 | Smith ...................................... 602/79 |
| 2,572,254 | 10/1951 | Folberth ......................... 128/206.18 |
| 3,461,733 | 8/1969 | Peterson ............................... 24/31 C |
| 3,653,381 | 4/1972 | Warnken ............................... 604/391 |
| 3,722,130 | 3/1973 | Handl .................................... 24/31 C |
| 4,463,757 | 8/1984 | Schmidt ......................... 128/205.29 |
| 4,622,034 | 11/1986 | Shattuck . |
| 4,665,566 | 5/1987 | Garrow . |
| 4,738,662 | 4/1988 | Kalt et al. . |
| 4,798,569 | 1/1989 | Alderfer ............................... 24/31 C |
| 4,821,736 | 4/1989 | Watson . |

Primary Examiner—Randall L. Green
Assistant Examiner—P. Zu Zuharelli
Attorney, Agent, or Firm—Louis T. Isaf

[57] ABSTRACT

An apparatus, along with a method for constructing and using the apparatus, which includes an absorbent dressing assembly wrapped around an elastic strap device which extends around a patient's head to secure the absorbent dressing assembly under the patient's nose to absorb nasal drainage. The elastic strap device includes two strap ends which define hollow openings for receipt of opposing ends of a coupling device having circular barbs for adjusting the distance between the strap ends, thus adjusting the size of a loop formed by the elastic strap device. The absorbent dressing assembly includes an absorbent dressing and a fastening hook patch affixed to the absorbent dressing to secure the absorbent dressing in a wrapped position around the strap device. The strap device further includes a restraining hook patch affixed to the strap device to releasably prevent the absorbent dressing from sliding relative to the strap device.

28 Claims, 1 Drawing Sheet

NASAL DRESSING SYSTEM

BACKGROUND OF THE INVENTION

The present invention relates generally to field of medical dressings, and in its most preferred embodiments, to the field of nasal mustache dressing systems.

It is well known that patients often experience nasal drainage or bleeding after various types of medical procedures. Medical personnel have employed various methods of absorbing these fluids. One of the most common methods includes securing a sterile mustache dressing under a patient's nose by applying adhesive tape to the dressing and to the patient's face. Although adhesive dressing systems are relatively effective, patients often experience much pain during removal of the dressings, and frequent dressing changes tend to produce very painful sores and skin irritations. Furthermore, medical personnel often spend considerable amounts of time changing adhesive dressings.

A more complicated method of securing a mustache dressing, included herein only as background information, includes utilizing a strap mechanism which loops around a patient's ears to bias a flat mustache bandage toward a position under a patient's nose. Although often less painful than the adhesive method discussed above, this strap method is often less reliable since the dressing tends to slip out from under the biasing strap and the entire device tends to slip off from a patient's ears during sleep.

There is a need, therefore, to provide a nasal dressing system which addresses these and other related, and unrelated, problems.

SUMMARY OF THE INVENTION

Briefly described, the nasal dressing system of the present invention, in its most preferred embodiment, includes an apparatus, along with a method for constructing and using the apparatus, which includes an absorbent dressing assembly wrapped around an elastic strap device which extends around a patient's head to secure the absorbent dressing assembly under the patient's nose to absorb nasal drainage. In the preferred embodiment, the elastic strap device includes two strap ends which define hollow openings for receipt of opposing ends of a coupling device having circular barbs for adjusting the distance between the strap ends, thus adjusting the size of a loop formed by the elastic strap device. The absorbent dressing assembly includes an absorbent dressing and, preferably, a fastening hook patch affixed to the absorbent dressing to secure the absorbent dressing in a wrapped position around the strap device. The preferred strap device further includes a restraining hook patch affixed to the strap device to releasably prevent the absorbent dressing from sliding relative to the strap device.

It is therefore an object of the present invention to provide a nasal dressing system which provides for painless dressing changes.

Another object of the present invention is to provide a nasal dressing system which provides for quick and convenient dressing changes.

Yet another object of the present invention is to provide a nasal dressing apparatus which is reliable and comfortable during use, including times of patient sleeping.

Still another object of the present invention is to provide a nasal dressing system which is easy to understand, use, and produce.

Still another object of the present invention is to provide a nasal dressing apparatus which includes an absorbent dressing and a support strap which extends completely around a patient's head.

Still another object of the present invention is to provide a nasal dressing system which utilizes disposable dressings removably wrapped around a portion of an elastic strap.

Still another object of the present invention is to provide a nasal dressing apparatus which includes a pliable tubular strap whose ends are connected to an adjustable coupler to form a loop for a patient's head.

Still another object of the present invention is to provide a dressing assembly for being wrapped around a support device, the dressing assembly including a dressing and a means for securing the dressing assembly in a wrapped position.

Other objects, features and advantages of the present invention will become apparent upon reading and understanding this specification, taken in conjunction with the accompanying drawings.

DETAILED DESCRIPTION OF THE PREFERRED EMBODIMENT

Figure 1:
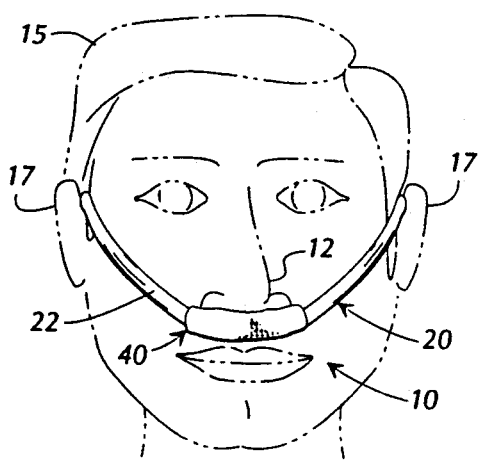
FIG. 1 is a front view of a nasal dressing apparatus in accordance with the preferred embodiment of the present invention shown positioned on a representative patient head.
Figure 2:
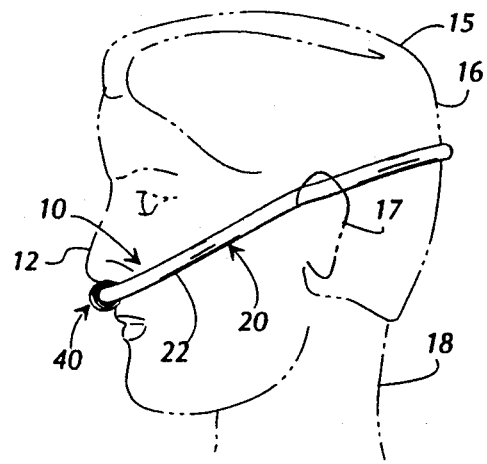
FIG. 2 is a side view of the elements shown in FIG. 1.

Referring now in greater detail to the drawings, in which like numerals represent like components throughout the several views, a nasal dressing apparatus 10, in accordance with the preferred embodiment of the present invention, is shown in FIGS. 1 and 2 positioned on a representative patient head 15. The nasal dressing apparatus 10 is shown including a support strap device 20 and an absorbent dressing assembly 40. The support strap device 20 is shown extending completely around the patient head 15 as it extends over two patient ears 17 and around head back 16. The absorbent dressing assembly 40 is shown supported by the support strap device 20 at a position under a patient nose 12.

Figure 3:
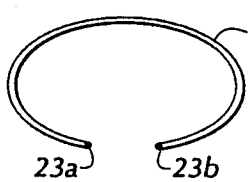
FIG. 3 is an isolated perspective view of an elastic tube in accordance with the preferred embodiment of the present invention.
Figure 4:
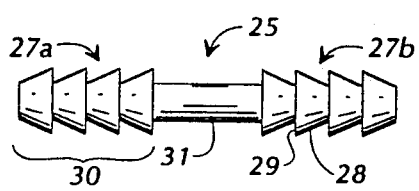
FIG. 4 is an isolated front view of a coupler in accordance with the preferred embodiment of the present invention.
Figure 5:
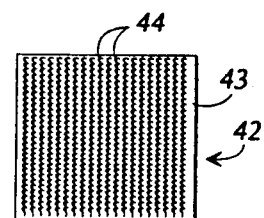
FIG. 5 is an isolated front view of a restraining hook patch in accordance with the preferred embodiment of the present invention.

FIG. 3 shows an isolated perspective view of an elastic tube 22 in accordance with the preferred embodiment of the present invention. The elastic tube 22 is hollow, soft, pliable and extends as a circular cylinder between circular tube openings 23a and 23b. FIG. 4 shows an isolated front view of a hollow coupler 25 in accordance with the preferred embodiment of the present invention. The coupler 25 includes opposing coupler ends 27a and 27b separated by a circular cylindrical coupler center 31. Each coupler end 27 includes a plurality of circular barbs 30. Each circular barb 30 is shown including a tapered barb incline 28 and a radially extending barb shoulder 29. FIG. 5 shows an isolated front view of a restraining hook patch 42 in accordance with the preferred embodiment of the present invention. The restraining hook patch 42 includes a patch base 43 and a plurality of patch hooks 44. In the preferred embodiment, the side of the patch base 43 opposite the patch hooks 44 (not seen) is coated with an adhesive. One example of an acceptable restraining hook patch 42 is the commercially available product commonly known as Velcro ® hook material.

Figure 6:
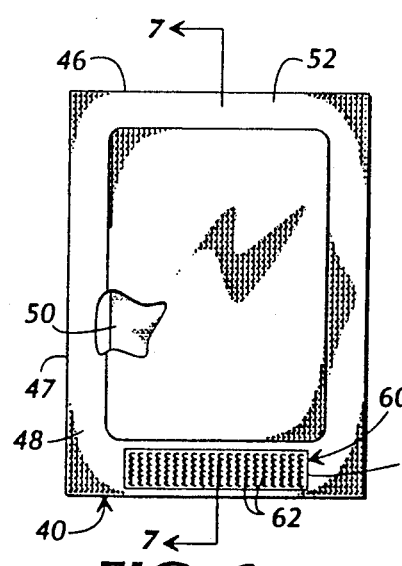
FIG. 6 is an isolated front view of an absorbent dressing assembly with a portion cut away for clarity and in accordance with the preferred embodiment of the present invention.
Figure 7:
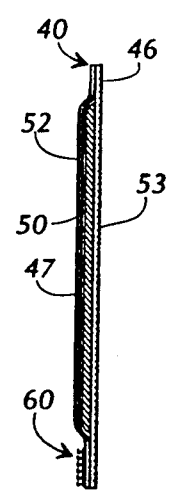
FIG. 7 is a cross-sectional view of the absorbent dressing assembly taken along line 7—7 of FIG. 6.

FIG. 6 shows an isolated front view of the absorbent dressing assembly 40 with a portion cut away for clarity and in accordance with the preferred embodiment of the present invention. FIG. 7 shows a cross-sectional view of the absorbent dressing assembly 40 taken along line 7—7 of FIG. 6. The absorbent dressing assembly 40 is shown including an absorbent dressing 46 and a fastening hook patch 60. The absorbent dressing 46 includes a gauze envelope 47 enclosing an absorbent pillow 50, thereby forming a gauze skirt 48 around the absorbent pillow 50. The gauze envelope 47 further includes a contact surface 52 and a fastening surface 53. The fastening hook patch 60 is adhesively affixed to a portion of the gauze skirt 48. The fastening hook patch 60 is shown including a patch base 61 and a plurality of patch hooks 62. As with the restraining hook patch 42 of FIG. 5, one example of an acceptable fastening hook patch 60 is the commercially available product commonly known as Velcro ® hook material.

Figure 8:
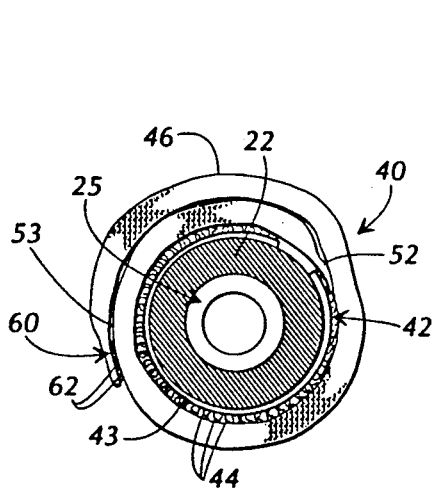
FIG. 8 is a side view of an absorbent dressing assembly encircling a portion of a support strap device, with the elastic tube shown in cross-section, in accordance with the preferred embodiment of the present invention.

FIG. 8 shows a side view of the absorbent dressing assembly 40 encircling the restraining hook patch 42, the elastic tube 22, (represented in cross-section) and the coupler 25, in accordance with the preferred embodiment of the present invention. The patch base 43 of the restraining hook patch 42 is adhesively affixed to the elastic tube 22. The patch hooks 44 are shown releasably connected to the contact surface 52 of the absorbent dressing assembly 40. The absorbent dressing 46 is shown secured in a wrapped position by the fastening hook patch 60 by virtue of the patch hooks 62 engaging the fastening surface 53 of the absorbent dressing 46. In the preferred embodiment of the present invention, the gauze envelope 47 is constructed of material having a plurality of loops, fibers, or strands which are capable of being releasably engaged by the patch hooks 44 and 62 of the restraining hook patch 42 and the fastening hook patch 60. Alternate embodiments of the present invention include alternate absorbent dressings 46 which do not include envelopes or multiple layers of material, but instead comprise one or more layers of absorbent material.

With reference to FIG. 2, in accordance with a preferred method of operation of the present invention, the nasal dressing apparatus 10 is first assembled and then positioned around a patient head 15 to absorb nasal drainage. According to an alternate method, the elastic tube 22 is first passed around the head back 16 of a patient head 15 before the nasal dressing apparatus 10 is assembled. Referring also to FIGS. 3 and 4, during assembly of the nasal dressing apparatus 10, each coupler end 27a,b of the coupler 25 is inserted into a tube opening 23a,b of the elastic tube 22 to form a continuous loop whose size is selectively dependant on the amount of coupler ends 27a,b inserted into the tube openings 23a,b. The barb inclines 28 do not hinder insertion of the coupler ends 27a,b, while the barb shoulders 29 tend to cooperate with the elastic tube 22 to restrict removal of the coupler ends 27a,b from the tube openings 23a,b. The patch base 43 of the restraining hook patch 42 (FIG. 5) is then adhesively affixed around the elastic tube 22 at the connection with the coupler 25, as shown in FIG. 8.

Referring now to FIGS. 6-8, after the support strap device 20 is assembled, the absorbent dressing assembly 40 is wrapped around the support strap device 20 at the restraining hook patch 42. Although alternate embodiments of the present invention include attaching the fastening hook patch 60 to the absorbent dressing 46 during assembly of the nasal dressing apparatus 10, in the preferred embodiment of the present invention, the absorbent dressing assembly 40 is pre-assembled as a sterile package such that the fastening hook patch 60 is firmly affixed to the gauze skirt 48 of the absorbent dressing 46 and the gauze envelope 47 securely encloses the absorbent pillow 50. To begin wrapping the absorbent dressing assembly 40 around the support strap device 20, the contact surface 52 is moved into engaging contact with the restraining hook patch 42. The restraining hook patch 42 acts as a restraining device to prevent the absorbent dressing assembly 40 from sliding with respect to the support strap device 20. An alternate embodiment of the present invention includes a continuous, pre-sized support loop without a coupler or a restraining device.

The absorbent dressing assembly 40 is then wrapped around the restraining hook patch 42 and then around the absorbent dressing assembly 40 itself. This wrapping continues for the length of the absorbent dressing 46. To secure the absorbent dressing assembly 40 in the wrapped position shown in FIG. 8, the patch hooks 62 of the fastening hook patch 60 are caused to engage the fastening surface 53 of the absorbent dressing 46. Also, as the absorbent dressing assembly 40 begins absorbing nasal drainage, the drainage itself helps to secure the absorbent dressing assembly 40 in the wrapped position. After the nasal dressing apparatus 10 is assembled, it is positioned around the patient head 15 (FIG. 2).

As the absorbent dressing assembly 40 becomes saturated with nasal drainage, or as routine medical procedures dictate, the old absorbent dressing assembly 40 is replaced with a new absorbent dressing assembly 40. According to a preferred method of the present invention, the nasal dressing apparatus 10 is slid downward to a position around a patient neck 18 (FIG. 2) before replacing the absorbent dressing assembly 40. In alternate methods, the nasal dressing apparatus 10 is completely removed from the patient head 15 before the absorbent dressing assembly 40 is replaced. To actually remove the absorbent dressing assembly 40, the absorbent dressing assembly 40 is unwrapped from the support strap device 20 by forcing the fastening hook patch 60 and the restraining hook patch 42 to release the absorbent dressing 46. A new absorbent dressing assembly 40 is then wrapped around the support strap device 20 as previously discussed, and the nasal dressing apparatus 10 is re-positioned around the patient head 15 (FIG. 2).

While the embodiments of the present invention which have been disclosed herein are the preferred forms, other embodiments of the method and apparatus of the present invention will suggest themselves to persons skilled in the art in view of this disclosure. Therefore, it will be understood that variations and modifications can be effected within the spirit and scope of the invention and that the scope of the present invention should only be limited by the claims below.

I claim:

1. A nasal dressing apparatus for attachment to a patient's head to absorb drainage from a patient's nose, said nasal dressing apparatus comprising:
   an absorbent dressing; and
   a strap means for extending completely around the patient's head to secure said absorbent dressing under the patient's nose,
wherein said absorbent dressing is wrapped all the way around at least a lengthwise portion of said strap means so as to surround said strap means to better secure said absorbent dressing under the patient's nose after said absorbent dressing has begun to absorb drainage.

2. Apparatus of claim 1, wherein said strap means includes, at least, an elastic strap.

3. Apparatus of claim 2, wherein said elastic strap defines a continuous ring.

4. Apparatus of claim 1, wherein said strap means includes, at least, a soft, pliable tube.

5. Apparatus of claim 1, wherein said strap means includes, at least, a strap first end and a strap second end, and wherein said dressing apparatus further comprises, at least, a coupling device interposed between said strap first end and said strap second end.

6. Apparatus of claim 5, wherein said coupling device includes, at least, an adjustment means for adjusting the relative positions of said strap first end and said strap second end.

7. Apparatus of claim 6, wherein said adjustment means includes, at least, a plurality of circular barbs.

8. Apparatus of claim 5, wherein said strap first end defines a first hollow opening, wherein said strap second end defines a second hollow opening, and wherein said coupling device includes, at least, a coupling first end for insertion into said first hollow opening and a coupling second end for insertion into said second hollow opening.

9. Apparatus of claim 1, further comprising a restraining means for restricting movement of said absorbent dressing relative to said strap means.

10. Apparatus of claim 9, wherein said restraining means includes, at least, a gripping element interposed between said strap means and said absorbent dressing.

11. Apparatus of claim 9, wherein said restraining means includes, at least, hook material affixed to said strap means.

12. Apparatus of claim 1, further comprising fastening means for removably securing said absorbent dressing in a wrapped position around said at least a portion of said strap means.

13. Apparatus of claim 12, wherein said fastening means includes, at least, hook material affixed to said absorbent dressing.

14. A nasal dressing apparatus for attachment to a patient's head to absorb drainage from a patient's nose, said nasal dressing apparatus comprising:
   an absorbent dressing;
   an elastic strap means for extending around the patient's head to secure said absorbent dressing under the patient's nose, said strap means including, at least, a strap first end defining a first hollow opening and a strap second end defining a second hollow opening;
   a coupling device interposed between said strap first end said strap second end, said coupling device including, at least,
      a coupling first end for insertion into said first hollow opening,
      a coupling second end for insertion into said second hollow opening, and
      an adjustment means for adjusting the relative positions of said strap first end and said strap second end, said adjustment means including, at least, a plurality of circular barbs;
   a restraining means for restricting movement of said absorbent dressing relative to said strap means, said restraining means including, at least, a gripping element interposed between said strap means and said absorbent dressing; and
   a fastening means for removably securing said absorbent dressing in a lengthwise wrapped position all the way around said strap means so as to surround said strap means in order to better secure said absorbent dressing under a patient's nose after said absorbent dressing has begun to absorb drainage.

15. Apparatus of claim 14, wherein said gripping element includes, at least, hook material affixed to said strap means.

16. Apparatus of claim 12, wherein said fastening means includes, at least, hook material affixed to said absorbent dressing.

17. A dressing apparatus for absorbing drainage comprising:
   a dressing support apparatus, and
   an absorbent dressing assembly removably wrapped all the way around at least a lengthwise portion of said dressing support apparatus device so as to surround said dressing support apparatus in order to better secure said absorbent dressing assembly along said dressing support apparatus after said absorbent dressing assembly begins to absorb drainage.

18. Apparatus of claim 17, wherein said dressing support apparatus includes, at least, an elastic strap including, at least, a strap first end and a strap second end, and a coupling device interposed between said strap first end and said strap second end.

19. Apparatus of claim 18, wherein said strap first end defines a first hollow opening, wherein said strap second end defines a second hollow opening, and wherein said coupling device includes, a least, a first plurality of circular barbs for insertion into said first hollow opening and a second plurality of circular barbs for insertion into said second hollow opening.

20. Apparatus of claim 17, wherein said absorbent dressing assembly includes, at least, an absorbent dressing and a fastening means for removably securing said absorbent dressing to said dressing support apparatus.

21. Apparatus of claim 20, wherein said fastening means includes, at least, hook material affixed to said absorbent dressing.

22. Apparatus of claim 20, wherein said fastening means includes, at least, hook material affixed to said dressing support apparatus.

23. A method of absorbing nasal drainage comprising the steps of:
- forming a support strap into a loop;
- connecting an absorbent dressing to the support strap by removably wrapping the absorbent dressing all the way around at least a lengthwise portion of the support strap so as to surround the strap in order to better secure the absorbent dressing along the support strap after the absorbent dressing begins to absorb nasal drainage;
- positioning the loop around a patient head; and
- positioning the absorbent dressing under a patient nose.

24. A nasal dressing apparatus for attachment to a patient's head to absorb drainage from a patient's nose, said nasal dressing apparatus comprising:
- an absorbent dressing;
- a strap means for extending completely around the patient's head to secure said absorbent dressing under the patient's nose, said strap means including, at least, a strap first end and a strap second end; and
- a coupling device interposed between said strap first end and said strap second end, said coupling device including, at least, an adjustment means for adjusting the relative positions of said strap first end and said strap second end, said adjustment means including, at least, a plurality of circular barbs, wherein said absorbent dressing is wrapped all the way around at least a lengthwise portion of said strap means so as to surround said strap means in order to better secure said absorbent dressing under the patient's nose after said absorbent dressing has begun to absorb drainage.

25. A nasal dressing apparatus for attachment to a patient'head to absorb drainage from a patient's nose, said nasal dressing apparatus comprising:
- an absorbent dressing;
- a strap means for extending completely around the patient's head to secure said absorbent dressing under the patient's nose, said strap means including, at least, a strap first end defining a first hollow opening and a strap second end defining a second hollow opening; and
- a coupling device interposed between said strap first end and said strap second end, said coupling device including, at least, a coupling first end for insertion into said first hollow opening and a coupling second end for insertion into said second hollow opening, wherein said absorbent dressing is wrapped all the way around at least a lengthwise portion of said strap means so as to surround said strap means in order to better secure said absorbent dressing under the patient's nose after said absorbent dressing has begun to absorb drainage.

26. A nasal dressing apparatus for attachment to a patient's head to absorb drainage from a patient's nose, said nasal dressing apparatus comprising:
- an absorbent dressing;
- a strap means for extending completely around the patient's head to secure said absorbent dressing under the patient's nose; and
- a restraining means for restricting movement of said absorbent dressing relative to said strap means, said restraining means including, at least, hook material affixed to said strap means, wherein said absorbent dressing wrapped all the way around at least a lengthwise portion of said strap means so as to surround said strap means in order to better secure said absorbent dressing under the patient's nose after said absorbent dressing has begun to absorb drainage.

27. A nasal dressing apparatus for attachment to a patient's head to absorb drainage from a patient's nose, said nasal dressing apparatus comprising:
- an absorbent dressing;
- a strap means for extending completely around the patient's head to secure said absorbent dressing under the patient's nose; and
- a fastening means for removably securing said absorbent dressing in a lengthwise wrapped position all the way around said strap means so as to surround said strap means in order to better secure said absorbent dressing under to patient's nose after said absorbent dressing has begun to absorb drainage.

28. A dressing apparatus for absorbing drainage comprising:
- a dressing support apparatus including, at least,
  - an elastic strap including, at least, a strap first end defining a first hollow opening and a strap second end defining a second hollow opening, and
  - a coupling device interposed between said strap first end and said strap second end, said coupling device including, at least, a first plurality of circular barbs for insertion into said first hollow opening and a second plurality of circular barbs for insertion into said second hollow opening; and
- an absorbent dressing assembly removably attached and wrapped all the way around a lengthwise portion of said dressing support apparatus so as to surround said dressing support apparatus in order to better secure said absorbent dressing assembly along said dressing support apparatus after said absorbent dressing assembly begins to absorb drainage.

* * * * *